US011246695B2

(12) United States Patent
Clément et al.

(10) Patent No.: US 11,246,695 B2
(45) Date of Patent: Feb. 15, 2022

(54) MEDICAL DEVICE COMPRISING AN ARTIFICIAL CONTRACTILE STRUCTURE

(71) Applicant: MyoPowers Medical Technologies France SAS, Besançon (FR)

(72) Inventors: Claude Clément, Prilly (CH); Marco Wieland, Basel (CH); Martin Horst, Horw (CH)

(73) Assignee: MyoPowers Medical Technologies France SAS, Besançon (FR)

(*) Notice: Subject to any disclaimer, the term of this patent is extended or adjusted under 35 U.S.C. 154(b) by 165 days.

(21) Appl. No.: 16/598,721

(22) Filed: Oct. 10, 2019

(65) Prior Publication Data
US 2020/0046480 A1 Feb. 13, 2020

Related U.S. Application Data

(60) Division of application No. 15/628,822, filed on Jun. 21, 2017, now Pat. No. 10,441,399, which is a (Continued)

(30) Foreign Application Priority Data

Dec. 23, 2011 (WO) .................. PCT/EP2011/073989

(51) Int. Cl.
*A61F 2/00* (2006.01)
*A61B 17/12* (2006.01)
(Continued)

(52) U.S. Cl.
CPC ...... *A61F 2/0036* (2013.01); *A61B 17/12009* (2013.01); *A61F 2/0045* (2013.01);
(Continued)

(58) Field of Classification Search
CPC ............................... A61M 1/10; A61M 17/12
(Continued)

(56) References Cited

U.S. PATENT DOCUMENTS 6,471,635 B1  10/2002  Forsell
7,011,621 B2   3/2006  Sayet et al.
(Continued)

FOREIGN PATENT DOCUMENTS

EP    1598030 A1   11/2005
JP    07-051304 A   2/1995
(Continued)

OTHER PUBLICATIONS

International Search Report, dated Jan. 23, 2013, from corresponding PCT application No. PCT/EP2012/076801.
(Continued)

*Primary Examiner* — Yashita Sharma
(74) *Attorney, Agent, or Firm* — Nixon & Vanderhye

(57) ABSTRACT

A medical device is provided including an artificial contractile structure which may be used to assist the functioning of a hollow organ. The medical device includes an artificial contractile structure including at least one contractile element configured to contract an organ, in such way that the contractile element is in a resting or in an activated position, at least one actuator configured to activate the contractile structure, and at least one source of energy to power the actuator. The medical device includes a corrosion reducing system configured to reduce corrosion of the medical device.

13 Claims, 5 Drawing Sheets

Related U.S. Application Data continuation-in-part of application No. 14/368,060, filed as application No. PCT/EP2012/076801 on Dec. 21, 2012, now Pat. No. 9,717,579.

(51) Int. Cl.
*A61M 60/268* (2021.01)
*A61M 60/892* (2021.01)

(52) U.S. Cl.
CPC ... *A61M 60/268* (2021.01); *A61F 2210/0014* (2013.01); *A61F 2230/0065* (2013.01); *A61F 2250/001* (2013.01); *A61F 2250/0007* (2013.01); *A61M 60/892* (2021.01)

(58) Field of Classification Search
USPC .............. 623/14.13, 24–26; 600/29–31, 37, 600/151–158; 606/201–202; 604/8–9; 417/410.1–417
See application file for complete search history.

(56) References Cited

U.S. PATENT DOCUMENTS

| | | |
|---|---|---|
| 2002/0040178 A1 | 4/2002 | Sayet et al. |
| 2002/0051550 A1 | 5/2002 | Leysieffer |
| 2003/0225311 A1 | 12/2003 | Sayet et al. |
| 2004/0054423 A1 | 3/2004 | Martin |
| 2004/0147801 A1 | 7/2004 | Kugler et al. |
| 2005/0148814 A1 | 7/2005 | Fischi et al. |
| 2006/0041309 A1 | 2/2006 | Massen et al. |
| 2008/0032828 A1 | 2/2008 | Alger |
| 2010/0204803 A1 | 8/2010 | Tozzi et al. |
| 2011/0015474 A1 | 1/2011 | Forsell |
| 2011/0063176 A1 | 3/2011 | Byrum et al. |
| 2011/0098731 A1 | 4/2011 | Whitbrook et al. |
| 2012/0184980 A1 | 7/2012 | Anderson et al. |

FOREIGN PATENT DOCUMENTS

| | | |
|---|---|---|
| WO | 99/18885 A1 | 4/1999 |
| WO | 99/48438 A1 | 9/1999 |
| WO | 02/26161 A1 | 4/2002 |
| WO | 2004/066879 A1 | 8/2004 |
| WO | 2007/066344 A1 | 6/2007 |
| WO | 2009/004092 A1 | 1/2009 |
| WO | 2009/048399 A1 | 4/2009 |

OTHER PUBLICATIONS

Richter et al., "Retropubic versus Transobturator Midurethral Slings for Stress Incontinence", The New England Journal of Medicine, 2010, vol. 362, No. 22, pp. 2066-2076.

MEDICAL DEVICE COMPRISING AN ARTIFICIAL CONTRACTILE STRUCTURE

TECHNICAL FIELD

The present invention relates to a medical device comprising an artificial contractile structure activated by an actuator, which may be advantageously used to assist the functioning of an organ, e.g. a sphincter or the heart. More generally, it can be used for moving or constricting a hollow or a tubular part of the body in such a way as to reduce its diameter.

BACKGROUND OF THE INVENTION

It is known to use artificial structures to assist muscular contraction. Such structures are adapted to assist atrial or ventricular contraction, or to assist or replace a natural sphincter. The use of such artificial sphincters has increased in recent years because faecal and urinary incontinences now affects more than 10% of people over 60 years of age and dramatically increases in patients over 80 years of age. Several pharmaceutical or surgical solutions have been developed for treating urinary and faecal incontinences. Generally, the outcome of surgery for treatment of urinary and faecal incontinence has to be regarded as low. The impacts on health care costs and overall quality of life of the patient are enormous.

The AMS800 artificial sphincter for urinary incontinence is commercialized by American Medical Systems and is composed of three components, a cuff, a pump, and a pressure-regulating balloon. The cuff is implanted at the bulbous urethra in males and is inflatable by means of a fluid. The pump is implanted in the scrotum and the pressure-regulating balloon is implanted in the abdomen. The major problems when using AMS800 is the tissue erosion around the urethra due to the constant pressure, the atrophy and irritation of tissues at the location of the inflatable cuff, and the emergency surgery for repair should the device remain in closed position in the event of mechanical failure. All other commercialized artificial sphincters whether for urinary or faecal incontinences bear similar drawbacks.

The ProAct™ device for urinary incontinence is commercialized by Uromedica and is composed of two small implantable balloons. During a short outpatient procedure, the balloons are surgically placed under the skin in the area where the prostate of the patient was surgically treated. The balloons help protect against accidental leaking of urine by increasing the amount of pressure required to urinate. When the patient needs to urinate, a normal amount of effort still should be required to push the urine out. However, the pressure from the balloons will help guard against unintentional urine loss, such as during a sneeze or cough. The major problems when using ProACT™ are identical to the problems using AMS800 artificial sphincter described above.

FlowSecure™, manufactured by Sterilin Ltd, another silicone hydraulic urinary sphincter similar to AMS800, has an extra pressure transmission balloon to transfer increased intra abdominal pressure directly to the cuff. Implantation of this device is technically feasible, but still difficult and is reported to be safe and effective in the short-term for the treatment of male urodynamic stress urinary incontinence, arising from a number of etiologies. However, the major problems when using FlowSecure™ are identical to the problems using AMS800 artificial sphincter described above.

Some publications describe the use of artificial sphincters comprising shape memory alloy elements suitable for opening and closing a part of an organ in a living body.

JP 07-051304 discloses a constrictor comprising two shape memory alloy elements with different shape memories, and covered by covering materials. The first covering material is formed in a shape to close the urethra in the daytime, and the second covering material is formed in a shape to half close the urethra in the night. This sphincter allows changing the pressure to the urethra, in order to prevent the incontinence in life action in the daytime, and to avoid necrosis of the tissue by loosing the pressure to the urethra in the night.

However, the drawbacks of such artificial sphincters are that there is a risk of tissue erosion and consequential necrosis, due to the high constant pressure to the urethra during the day and that there is a risk of incontinence during the night. If the shape memory alloy is no more efficient or is broken, the whole sphincter should be moved and replaced. Another risk is tissue erosion due to the high temperature of the shape memory alloy.

Moreover, JP 07-051304 discloses an artificial sphincter in which the shape memory alloy elements are disconnected from each other. This embodiment does not allow optimal pressure control.

Moreover, this kind of shape memory alloy elements uses a lot of power. That means that the battery needs to be changed very often or alternatively very large batteries have to be used.

EP 1 598 030 discloses an urine incontinence treatment apparatus, comprising a restriction device for engaging the urethra to form a restricted urine passageway in the urethra, the restriction device being operable to change the restriction of the urine passageway, a source of energy, and a control device operable from outside the patient's body for controlling the source of energy to release energy for use in connection with the operation of the restriction device, a motor or pump implantable in the patient, wherein the source of energy is adapted to power the motor or pump and the control device is adapted to control the motor or pump to operate the restriction device. The source of energy can be an internal battery with a lifetime of at least 10 years. However, as disclosed in EP 1 598 030, an internal battery is an advantageous solution for embodiments of the apparatus that have a relatively high consumption of energy, which cannot be satisfied by direct supply of wireless energy. Therefore, even if the lifetime of the internal battery is of 10 years, the operation time of said internal battery is shorter as the energy consumption is very high. Said internal battery should therefore be changed very often.

WO 2009/048399 discloses an apparatus for controlling a flow of sperms in an uterine tube, comprising an implantable flow influence device to be applied on at least one portion of the uterine tube. The energy source is an implantable primary battery or accumulator. Preferably the energy source is external and a control device controls the external energy source to transmit wireless energy from the outside of the patient's body to the inside. The energy will directly be used or the operation of the device e.g. to power the constriction/stimulation unit. The internal source may store energy. The constriction/stimulation device needs high energy to be activated but also to be maintained in an activated position. Therefore the preferable energy supply is the wireless transmission of energy. A drawback of wireless transmission is its efficiency. In case of using an accumulator for storing energy the accumulator has to be recharged frequently that reduces the lifetime of the accumulator.

WO 2009/004092 discloses an artificial structure comprising several contractile elements adapted to contract an organ by means of contractile fibers. Such fibers need high energy to be activated but also to be maintained in an activated position. As disclosed in WO 2009/004092 an implanted rechargeable battery needs to be recharged at least once a day using a battery volume in the range of this invention. Larger rechargeable batteries with more capacity exist but would not be possible to implant.

WO 2004/066879 discloses a male sexual impotence treatment apparatus, comprising a constriction member extending in a loop around the penile tissue. Wireless energy transfer is used to electrically power the constriction member during device operation that means external energy is wireless transmitted from the outside of the patient's body to the inside to recharge the implantable battery. The energy will directly be used or the operation of the device or to recharge the battery. The actuator is fixed on the constriction member in such a way that an electric wire linking the actuator to a source of energy goes through the body of the patient. A drawback of wireless transmission is its efficiency. Another drawback is the recharging of the battery. Small rechargeable batteries have to be replaced after about 1 year. Moreover, the electric wire should be designed to conduct a current in the order of milliamperes, which is needed for powering the operation device when operating the constriction device, so that the constriction device exerts a force strong enough to constrict the penile tissue or the prolongation thereof, so that the patient's penile exit blood flow is restricted. Thus the electric wire should have a low resistance.

No information is given, how much energy is needed to constrict the penile tissue and for how long. Based on the description and the drawings, continuous power is needed to hold the device in constrict position.

WO 2007/066344 discloses an implantable extra cardiac compression device for left ventricular assistance in severe heart failure. The device comprises metal flanges that are passively flexed at springed-hinges by a vertically moving metal cup. The flanges are connected to each other by a high-tensile, elastic polymer membrane. However, with such device, one flange, used alone, cannot contract the organ. Moreover, such device needs high energy to be activated but also to be maintained in an activated position. The external battery that may be recharged will be connected transcutaneously to the motor assembly placed inside the patient's abdomen. A transcutaneous connection always bears a risk of infection.

Moreover, when such implantable devices are placed in the body of a patient, they are on contact with body fluids. Moisture penetrates into the device and more specifically into the control unit and the actuator. Moisture condenses, and water propagates and reaches the control unit, in which corrosion starts. The drawback is that some parts are corroded, and more specifically, the electronic and mechanical parts of the control unit and the actuator.

U.S. Pat. No. 7,011,621 discloses a body fluid flow control device comprises a first engaging element and a second engaging element (called plunging member) forming an inner diameter when second member moves towards first member to encircle a body vessel. That means the plunging member moves and press one side of the organ. With other words motor drives the worm gear pulling the nut along with the casing and thus acts on the cable to push the plunging member to close the body fluid flow control or to pull on the plunging member using the cable to open the body fluid flow control. The described design has several disadvantages. First pushing the plunging member needs a quite stiff cable to apply the necessary pressure towards the vessel. Otherwise the cable would kink. Patient feels stiff sleeve including cable. The bending radius of a stiff cable is limited. This will limit the indications, e.g. the implantation of such a device close to the bladder neck is almost impossible. Second the inner diameter that is formed when the plunging member is moved towards the first engaging member is just in one limited case a circle, namely when the radius of the first engaging member and the plunging member are the same. Otherwise, and this will be the normal case using this design the enclosing form is like a lens or an oval leading to not evenly distributed pressure on the vessel. That means there are areas where the tissue will be compressed more than in other areas leading to tissue damage. Further the circumference of the vessel could be much bigger that the circumference built by the two members. That means that by moving the plunging member towards the first member vessel will be squeezed without being closed resulting in tissue damage. On the other hand the circumference of the vessel could be smaller than the circumference of the two members meaning that the vessel stays open, even the members are closed. Further, the vessel is pressed all the time except when e.g. the patient has to void. This leads to the same problem as for AMS 800 namely to tissue erosion around the vessel due to the constant pressure, the atrophy and irritation of tissues.

The disclosed concept is very energy consuming because energy is needed to maintain the closed position. There is no mechanism described that would keep the device in its closed position. Moreover in case of no power the closed position of the members cannot be hold because of vessel pressure and the motors turn back to a balanced position. But in this position the vessel is not closed anymore.

Moreover, U.S. Pat. No. 7,011,621 discloses the use of a magnetic coupling device placed between the casing and the cable. In this configuration, the magnetic field is not well shielded. That means that the magnetic field of the magnets will influence the reliability of the electromotor.

WO 99/48438 discloses an artificial sphincter system which comprises a first shell and a second shell for coupling with the second shell to form a cylindrical objective suitable for engaging and surrounding a selected canal with the host body. It also includes a plunger for constricting the fluid flow when activated. The host-user can activate the sphincter system with a remote control. The device also comprises a casing containing a piston-like mechanism for driving a plunger into the hollow portion of the device to restrict fluid flow through the canal enveloped by the device. The piston-like mechanism is preferably an electromechanical solenoid but any hydraulic, pneumatic, or equivalent piston-like mechanism can be used.

Piston-like or plunging member need power be stay in closed position. No information is provided about how much energy (current) is needed to open and close the piston-like or plunging member and keep closed position meaning continuous current would be needed to keep the sphincter closed.

US 2005/148814 discloses an electromechanical apparatus and method useful for augmenting muscle function. The method involves operating electrically operated actuators on an external surface of the muscle or organ. The carrier comprises electrically operated actuators arranged in a band, mesh, or other suitable arrangement. In some embodiments of the invention, the carrier has a band-like, tubular or cuff-like shape that facilitates the carrier at least partially encircling the organ.

The control system includes a (Analog-to-digital) ADC conversion system which provides processor system with digital signals corresponding to the analog bioelectronic signals picked up from the organ by electrode. The control system includes also a (Digital-to-analog) DAC system which provides carrier with analog signals that causes it to compress and relax in response to the digital output signals computed processor system.

This means that the apparatus needs to be regularly powered.

Moreover, in operation, in essentially the manner of a conventional solenoid, currents in wire coils create magnetic fields and corresponding forces upon magnetized members. The resulting movement of the members contract the mesh of actuators causing carrier to compress the organ to which it is applied. When the current is removed, the mesh expands again.

That means that a continuous current is needed for compressing the organ.

Therefore there are, at the present time, no adequate solutions, whether commercial or in the literature, for implanting robust devices comprising an artificial contractile structure.

SUMMARY OF THE INVENTION

The present invention provides an implanted medical device comprising an artificial contractile structure which allows to avoid the disadvantages of the prior art.

Accordingly, the present invention relates to a medical device comprising:
- an implantable artificial contractile structure comprising at least one contractile element adapted to contract an organ, in such way that said contractile element is in a resting or in an activated position, the activated position being defined with said contractile element constricting the organ and the resting position being defined with said contractile element not constricting the organ,
- at least one actuator designed to activate said contractile structure,
- at least one control unit comprising and controlling said actuator, and
- at least one source of energy for powering said actuator.

According to the invention, the contractile element comprises a band which surrounds at least partially the organ to be contracted, said band comprises a free end designed to cooperate with locking means, said locking means being able to adjust the band to the size of the organ.

Advantageously, the control unit comprises a titanium housing with at least a first chamber and at least a second chamber and means for reducing corrosion in the control unit, said means for reducing corrosion comprising a thin titanium wall constituting a flat hermetic wall between said first and second chamber.

Advantageously, the present invention provides a medical device comprising an artificial contractile structure which is designed for chronic applications (i.e. long-term implantation), for example for many months and preferably many years.

Such devices may be used in several indications, e.g. for assisting or replacing a natural sphincter, especially for the treatment of faecal or urinary incontinence, for assisting atrial or ventricular contraction, for assisting the respiratory function, for assisting or replacing a paralyzed muscle or for treating venous insufficiency. The present invention is particularly designed for improving sphincter muscle function and therefore to improve the patient's quality of life with a significant reduction of treatment costs.

DETAILED DESCRIPTION

Figure 1:
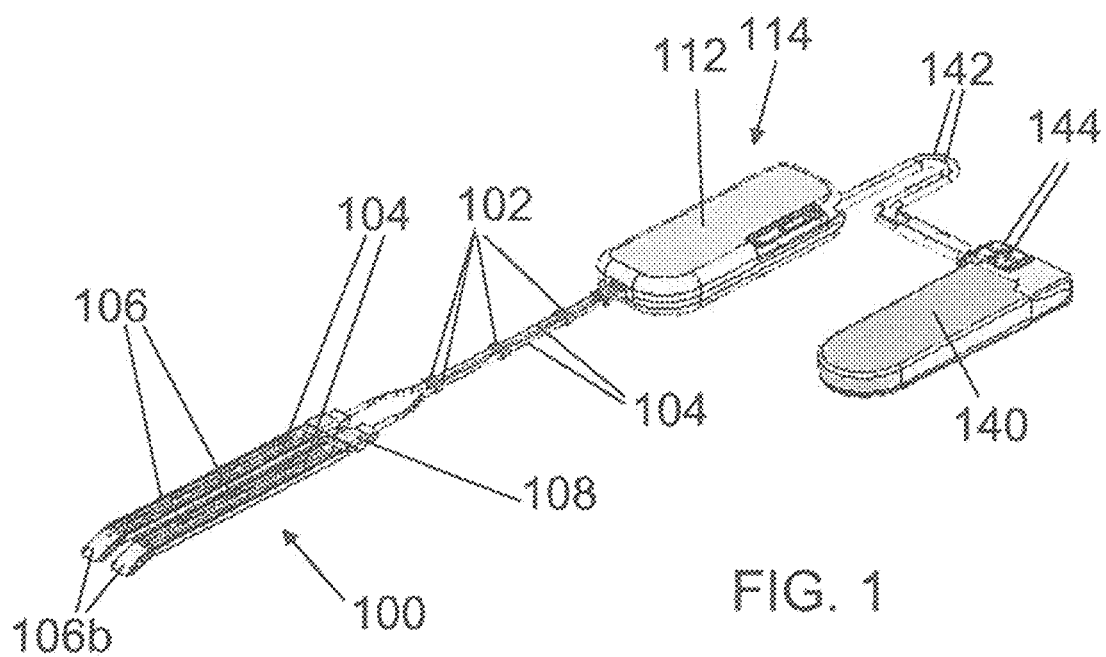
FIG. 1 is a schematic view of a medical device according to the present invention.

In the present description, the term "organ" covers any organ of the human body, preferably an organ comprising a hollow part, containing fluids as for example the ventricular part of the heart, or a region of an organ in the living body having an overall cylindrical shape, for example a blood vessel, the urinary tract, the colon, the stomach or any other body part against which pressure can be applied.

In the present description, the term "electromotor" covers any device designed to produce motion and mechanical effects by the action of electricity.

In the present description, the term "constrict" means that the contractile element applies a pressure against a region of an organ around or on which said contractile element has been placed.

In the present description, the term "pulsatory" means that each contractile element is activated and deactivated in alternation with another contractile element to constrict or apply a pressure or not against the region of the organ or the hollow part around or on which it has been placed, preferably so as to close or open said region of the organ or of the hollow part. More especially, in a preferred embodiment, contractile element one is closed for a certain time, while the other contractile element(s) are open. After a given time the contractile element two will be closed while the contractile element one is still closed. When contractile element two is closed, contractile element one opens, and so on. The frequency of alternate activation is dependent upon the nature of the tissues and inside organ pressure, and is adjusted so that no tissue erosion and burn appear after several months of implantation.

In the present description, the term "continuous" means that a pressure is applied against at least one region of the organ in such a way that said organ is closed during all the time for which the medical device is used, except the short periods for which the organ should be open.

In the present description, the term "link" means a direct or indirect connection between two elements.

The medical device comprises:
- an artificial contractile structure comprising at least one contractile element adapted to contract an organ, in such way that said contractile element is in a resting or in an activated position, the activated position being defined with said contractile element constricting the organ and the resting position being defined with said contractile element not constricting the organ, at least one actuator designed to activate said contractile structure and separated from the contractile structure, at least one control unit comprising and controlling the actuator, at least one source of energy for powering said actuator.

Preferably, said actuator comprises at least one electromotor provided with a gearhead and transmission means linked to the contractile element and designed to transmit to the contractile element a force induced by the electromotor.

Advantageously, the actuator is separated from the contractile structure. That means that the actuator is linked to but not fastened on the contractile structure or on the contractile element.

According to the present invention, said medical device further comprises means for reducing corrosion, and more particularly in the control unit.

One of these means for reducing corrosion in the control unit consist in that the control unit comprises at least one first chamber, which is hermetically sealed and contains elements which are the most sensitive to moisture, as for example the electromotor and its gearhead, and on its side facing the contractile element, at least one second chamber, which is not hermetically sealed and which contains a part of the transmission means.

The first chamber may also contain other electronics, as printed circuit boards and position sensors.

The second chamber is designed in such a way that the transmission means exit from said second chamber in direction of the contractile element.

Advantageously, the first chamber is sealed to the walls of the second chamber by means of a laser seam weld. The first and second chamber may be made of titanium.

The first and second chambers may be placed in the same housing, made for example of titanium.

According to another embodiment, this housing may further comprise a third chamber, which is also hermetically sealed and may contain elements which are sensitive to moisture and which are not placed in the first chamber.

In this embodiment, the electromotor and its gearhead may be placed in the first chamber, and electronics as printed circuit boards and position sensors may be placed in the third chamber.

The elements which are placed in the first and/or third hermetically sealed chambers are not necessary made of biocompatible material.

Having the motor and its gearhead placed in the first chamber and the electronics placed in the third chamber has the advantage to use a brush motor. Indeed in that case, dust coming from the brushes will remain in the first chamber and cannot interfere with the electronics placed in the third chamber. Brush motors have the advantage that they have the simpler electronic which make them more reliable.

Advantageously, the actuator further comprises a magnetic coupling device designed to transmit to the contractile element a force induced by the electromotor. Preferably, said magnetic coupling device is placed at the end of the gearhead of the electromotor.

Preferably, said magnetic coupling device comprises a first magnet placed in the first chamber and a second magnet placed in the second chamber. The thin titanium wall of the second chamber, which separates the first magnet from the second magnet, constitutes a flat hermetic seal. The magnets may be placed advantageously on each side of said flat hermetic seal, one behind the other. The use of flat surfaces allows having simple design which is easy to produce, contrary to the design disclosed in U.S. Pat. No. 7,011,621. The magnets may be encapsulated, for example in titanium.

Moreover, advantageously, the magnetic field of the magnets that are on each side of the flat seal can be reduced with metal plates to avoid any dysfunction of the electromotor. Shielding the magnetic fields requests a proper position of the Hall sensor which may be used as position sensor, close to the second magnet because of the reduced magnetic field. More than one Hall sensor could be placed.

In a preferred embodiment, the actuator may comprise an electric motor, a gearhead connected to said motor, a lead screw and a nut mounted on said lead screw, one of the nut and the lead screw being linked to said transmissions means and the other of the nut and the lead screw being designed to cooperate with said gearhead.

Advantageously, the lead screw, the nut and a part of the transmission means are placed in the second chamber and the electric motor and the gearhead are placed in the first chamber, in such a way that moisture is confined in a restricted area around the lead screw and in such a way that the electric motor and the gearhead are not exposed to moisture and not corroded. No specific measures against corrosion are needed.

Advantageously, the magnetic coupling device is designed to transmit the movement of the gearhead in the first chamber to one of the nut and the lead screw placed in the second chamber.

In one embodiment, the lead screw is a rotating lead screw designed to cooperate with the gearhead via the magnetic coupling device, and the nut is mounted on said lead screw and linked to the transmission means. More specifically, the first magnet is placed on a pin at the end of the gearhead and the second magnet is placed at the end of the lead screw. When the motor turns, the first magnet rotates and transmits rotation to the second magnet that rotates the lead screw. The lead screw transmits the rotational movement into axial movement of the nut and finally the transmission means.

In another preferred embodiment, the nut is a rotating nut designed to cooperate with the gearhead via the magnetic coupling device, and the lead screw, on which the rotating nut is mounted, is a linear lead screw linked to the transmission means. More specifically, the first magnet is placed on a pin at the end of the gearhead and the second magnet is placed at the end of the rotating nut facing to the gearhead. When the motor turns, the first magnet rotates and transmits rotation to the second magnet that rotates the nut. The nut transmits the rotational movement into axial movement of the lead screw and finally the transmission means.

Optionally a third magnet is mounted on a metal plate that shields magnetic fields from the first magnet. This metal plate is the support for the first and third magnet.

This third magnet is used for the position sensing by using for example two Hall sensors mounted at the front of the gearhead. With this embodiment, the sensitivity of the Hall sensors is increased.

The transmission means may be mechanical, hydraulic, electromechanical or pneumatic. Preferably, the transmission means may be a cable linking one of the lead screw and the nut to the contractile element.

Advantageously, in the preferred embodiment comprising the rotating nut and the lead screw, the transmission means may be linked to the center of the lead screw. Therefore there is no twist force between the screw and the nut, in such a way that the wear and the risk of blocking the nut decrease.

The cable may be protected by a coaxial sheath. The sheath can be made for example of silicone, polyimide, PTFE composites (PTFE and fluoroethylkene polymers), pure PTFE, or other appropriate polymers. The sheath can be additionally coated with silicone, if necessary. In other embodiment, the cable may be surrounded by a silicone tube. Cables are well known in surgery. As in the present invention one pulls on the cable to close the contractile element, a stiff cable is not required. Then bending up to 10 mm radius is possible. It could be a Teflon® cable in a Teflon® tube to reduce the friction. The cable could be woven out of several cables to be more flexible and to reduce risk in case of cable break.

The cables can be made for example out of polyamide like Nylon®, polyether block amide, PTFE, or other appropriate polymers. Alternatively, other materials, as stainless steel or titanium, can be used. Surgeon is used to place cables in the human body.

The resting position of the contractile element of the structure corresponds to a state in which any force is transmitted by the transmitting means to the contractile element, and the activated position corresponds to a state in which a force has been transmitted in such a way that the contractile element closes and constricts the organ to be contracted.

In some embodiments, the contractile element is made out of biocompatible materials, preferably selected from the group consisting of silicone, PTFE composites (PTFE and fluoroethylkene polymers), pure PTFE, polylactide (PLA)-polymer, polyurethane (PUR), Polymethylmethacrylate (PMMA), polyoxymethylene (POM), HDPE polyethylene and LDPE polyethylene or combinations thereof. Other appropriate material as other polymers or metal can be used.

The contractile element of the contractile structure may have the form of an open ring to be placed around the organ or around a hollow part of the organ to be contracted, said ring having a moving part linked to the transmitting means.

Preferably, the contractile element comprises a moving part linked to the actuator and designed to move, when activated by the actuator, between the activated position and the resting position of the contractile element.

Advantageously, the contractile element comprises a band which surrounds at least partially the organ to be contracted, and the transmission means are designed to be linked to the band and to pull it, when the contractile element is activated by the actuator, in such a way that said contractile element reaches its activated position.

Preferably, at least a part of the transmission means is integrated in said contractile element, such embodiment corresponding to means for reducing corrosion in the control unit. By this way, the contractile element and the transmission means form only one member. As a part of said transmission means is integrated in the contractile element, there is neither opening nor interface between the contractile element and the transmission means. Therefore, no body fluid can directly flow along the transmission means into the control unit. Therefore, corrosion of electronic and mechanical parts in the control unit and in the actuator can be significantly reduced. Moreover, it will also prevent that part of the body fluid glue the cable.

Advantageously, the contractile element is a band in which the transmission means, and more specifically the cable coming from the actuator are embedded.

The band may be a U-shaped band or a larger flat band. The U-shape allows stabilizing the contractile element when closing whereas a larger flat band means that the contractile element is in contact with a larger surface contact area of the organ, which is more tissue friendly.

In one embodiment, the transmission cable is surrounded by a sleeve, as a Teflon® tube, which is in its turn embedded in a U-shaped band, made for example of silicone.

In another embodiment, said sleeve is flat and is itself the larger band in which the transmission cable is embedded. The band may be made of Teflon®.

The sleeve is designed to act as a guiding spring allowing axial constrict of the contractile element when it is pulled from resting or open position to activated of close position. Such spring has another advantage by the contractile element opening, only about 30 to 40% of the closing energy being needed. The sleeve may be advantageously made of expandable Teflon®.

Advantageously, the locking means are able to adjust the band so as the contractile element reaches the resting position where the band is surrounding the organ without applying any surface pressure to the organ.

One end of the contractile element is linked to the transmission means coming from the actuator and its other end is free and designed to cooperate with locking means to fix this free end to the band.

The locking means are designed to fix the free end of the band to another part of the band, said band forming a loop around the organ.

In one embodiment, the locking means are a click mechanism. The free end of the band is made from PEEK, POM or similar biocompatible material which is able to slide through a movable cover forming a locking member made also from PEEK, POM or similar biocompatible material until the position is reached where the band is surrounding the organ without applying any surface pressure to the organ. In this position, the free end of the band is clicked into the locking member. The free end of the band is protected with a silicone lip to guarantee that the organ is in contact only with soft silicone. The free end of the band is undercut allowing movable cover to be clicked. The cable may be fixed in the free end by using for example a ball.

In another embodiment, the locking means are a snap mechanism. The free end of the band is designed to cooperate with a grid provided on the other end of the band to close the contractile element.

Advantageously, a X-ray or CT marker may be incorporated into the band of the contractile element in such a way that the position of said contractile element could be detected.

Advantageously, markers for circumference could be added in the contractile element. This allows the physician to measure the organ and place the band around the organ and moves it until the corresponding marker is reached. Then the locking means are activated.

As a part of the transmission means is integrated in the contractile element, the size of the contractile element is able to be adjusted to the size of each individual organ with only one size of band. There is no need of some prefabricated sizes of band.

In some embodiments, the size of the band may be comprised between 3 cm and 15 cm in length, preferably between 3 cm and 12 cm in length, and between 3 mm and 15 mm in width, preferably between 3 mm and 12 mm in width.

The actuator may further comprise sensors designed to indicate the position of the transmitting means or the force applied by the actuator. Preferably, such sensors are Hall sensors. Such sensors are preferably placed in the first or the third hermetically sealed chamber close to the second magnets in the second chamber. In another preferred design, such sensors are placed in the first chamber at the front of the gearhead.

Advantageously, the source of energy has a volume less than 20 cm$^3$, preferably less than 15 cm$^3$ and most preferably less than 12 cm$^3$.

Moreover, the ratio "current which is needed to maintain the contractile element in its activated position and in its resting position/current which is needed to change the position of the contractile element" is less than $1/500$, preferably less than $1/800$, and more preferably less than $1/1000$. Preferably, the ratio "current which is needed to maintain the contractile element in its activated position and in its resting position/current which is needed to change the position of the contractile element" is comprised between $1/20000$ and $1/500$, preferably between $1/14000$ and $1/800$, and more preferably between $1/8000$ and $1/1000$.

Advantageously, the actuator comprises actuating means (preferably the screw/nut system) designed in such a way that the energy consumption of said medical device which is needed to change the position of the contractile element and to move it between its activated position and its resting position is less than 2000 mAh/year and preferably less than 1800 mAh/year and in such a way that the energy consumption of said medical device which is needed to maintain the contractile element in its activated position is less than 200 mAh/year for a continuous pressure applied on the organ by the contractile element, which is in its activated position, comprised between 0.1 N/cm$^2$ and 5 N/cm$^2$. Preferably, this pressure is applied alternatively through independent contractile elements.

Preferably, said actuating means are designed in such a way that the energy consumption of the medical device which is needed to change the position of the contractile element is less than 1350 mAh/year and in such a way that the energy consumption of said medical device which is needed to maintain the contractile element in its activated position is less than 150 mAh/year for a continuous pressure applied on the organ by the contractile element, which is in its activated position, comprised between 0.3 N/cm$^2$ and 2.5 N/cm$^2$. Preferably, this pressure is applied alternatively through independent contractile elements.

Advantageously, the current consumption of the medical device of the invention which is needed to change the position (moving between the activated position and the resting position) of the contractile element for five years is comprised between 350 mAh and 9000 mAh, preferably between 350 mAh and 6750 mAh, and the current consumption of said medical device which is needed to maintain the contractile element in its activated position is comprised between 75 mAh and 1000 mAh for a continuous pressure applied on the organ by the contractile element, which is in its activated position, comprised between 0.1 N/cm$^2$ and 5 N/cm$^2$, preferably between 0.3 N/cm$^2$ and 2.5 N/cm$^2$. Preferably, this pressure is applied alternatively through independent contractile elements.

The source of energy can be implantable or placed outside the body of the patient.

In one embodiment, the actuator and its control unit, and the source of energy are implantable and are placed in the same closed box, separated from the contractile structure or from the contractile elements.

In a preferred embodiment, the control unit and the source of energy are separated in two boxes (control unit and power supply unit) and connected with an electric cable, which should be easily detachable. A direct current (DC) can be used between the power supply unit and the control unit. In a preferred embodiment, one uses means for providing a current conversion DC/AC (alternative current)/DC between the power supply unit and the control unit. Such embodiment allows to reduce the corrosion of the cables connecting the power supply unit and the control unit. Therefore the means for providing a current conversion DC/AC/DC between the power supply unit and the control unit are also means for reducing corrosion of the medical device.

In other embodiments, the actuator and its control unit is implantable and the source of energy is placed outside the body of the patient. In some embodiments, the source of energy comprises at least one implantable rechargeable battery with an implantable antenna and an external battery. Such implantable battery is for example a Lithium-Ion or Lithium Polymer rechargeable battery commercialized by GreatBatch and others. The energy transfer system that is needed to recharge the battery, is preferably through wireless connection. Such system can comprise a recharge unit, as a belt, comprising an external battery. The patient should wear the recharge unit for a number of hours to recharge the implanted battery. The energy should be transmitted wireless to the implanted battery via appropriate antenna. The system can also comprise a cradle for charging the recharge unit. Charging can be performed through a wired or metal contact connection. The battery provides sufficient energy for at least 1 month operation of the medical device. Recharge time is less than 6 hours. In another preferred embodiment, the source of energy is at least one implantable primary (i.e. non-rechargeable) battery, having advantageously a lifetime of at least 4 years for a volume of 3.7 cm$^3$ (in total 7.4 cm$^3$ if two batteries are used). The battery may be a lithium-manganese dioxide battery.

The battery volume and weight are crucial for implantable devices. Therefore a high power density is needed. Larger batteries with lower power density exist. But if these batteries are too big and heavy, they cannot be implanted. The devices would become too large and e.g. visible under the skin. Further it is not always possible to fix the device in the body. Therefore there is a risk of implant movement due to high weight of the device. Heavy devices could be not comfortable for the patient. Moreover, too large and heavy batteries could be the reason to exclude a device for a particular therapy.

The features of the battery depend on the application of the artificial structure, on the pressure to be applied, on the number of contractile elements to activate, and how often the patient opens and closes the contractile structure.

In the present invention, when energy is provided to the electromotor, this energy may be transmitted, via the magnetic coupling device which is placed between the electromotor and the lead screw/nut system, to one of the lead screw and the nut, which converts its rotation movement to a lateral or axial movement of the other of the lead screw and the nut. When the nut or the lead screw moves axially, it pulls or pushes the cable to close or open the contractile element. No extra release mechanism is required. No or minimal energy is needed to maintain the contractile element in its activated position due to the self-locking lead screw design, which means that the maximum pressure on the organ is maintained with minimal energy consumption. Moreover, no or minimal energy is needed to maintain the contractile element in its resting position due also to the self-locking lead screw design. In the case corresponding to minimal energy consumption, only a few electronic components on the printed circuit board are permanently powered, mainly for communication purpose with the remote controls.

Most energy is needed for just a few seconds to move the screw/nut system and close and open the contractile element which also provides significant reduction of the power consumption that allows a significant increase in the battery life time.

The cycle of a contractile element of the invention is that no energy is provided to maintain the contractile element in its resting position, some energy is needed for just a few seconds to move the nut and close the contractile element until its activated position, then no energy is provided to maintain the contractile element in its activated position, and then some energy is needed for just a few seconds to move the nut and open the contractile element until its resting position. Therefore, no continuous energy is needed in such a way that the contractile element is maintained in its activated or resting position. The total energy consumption is then very low.

Moreover, due to the use of a spring sleeve in which the cable is inserted, the device of the invention needs only about 30 to 40% of the closing energy to open the contractile element.

With such lower energy consumption, which was never disclosed in the prior part, the operation time of the battery used as source of energy is comprised between 1 month and 10 years, preferably between 1 year and 10 years, and more preferably between 2 years and 8 years, optimally 5 years, for a battery having a volume of 3 $cm^3$ to 20 $cm^3$.

The medical device of the invention allows therefore the use of a primary battery placed inside the body of the patient, which is to be changed only several years after its implantation, optimally 5 years for a battery having a volume of 3 $cm^3$ to 20 $cm^3$. Therefore the medical device of the invention need no accumulator or rechargeable battery, which is an advantage compared to the devices of the prior art.

Moreover, the motor, the gear ratio and the lead screw/nut system have been chosen in such a way that the travel time needed by the nut for moving along the lead screw and the lead screw moving in case of rotation nut between the resting position and the activated position is comprised between 0.2 s and 90 s, for a travel of the nut comprised between 2 mm and 50 mm, preferably between 3 mm and 15 mm. Preferably, the travel time needed by the nut or the lead screw, respectively for moving between the resting position and the activated position is comprised between 0.4 s and 60 s, more preferably between 0.5 s and 10 s, and more preferably between 0.5 s and 5 s for a travel of the nut or the lead screw respectively comprised between 2 mm and 50 mm, preferably between 3 mm and 15 mm.

The time for opening or closing the contractile element could be different and depends on the material of the contractile element.

The appropriate electromotor is commercialized for example by Maxon Motor AG, Faulhaber or Portescap. Preferably, the gear ratio is comprised between 4 and 64, and preferably between 12 and 64. The lead screw has a pitch comprised between 0.2 mm and 3 mm, preferably between 0.3 mm and 2 mm, and more preferably between 0.4 mm and 1 mm and an effective diameter comprised between 1 mm and 4 mm. Leadscrews with metric threads, for example with a thread angle of 60°, could be used. Preferably, the leadscrew has trapezoidal threads, for example with a thread angle of 30°. This configuration allows to obtain better yield.

The following strategies have been worked out to reach a high efficient and power saving device.

First, the requirements for battery system in implant should be a very high power density, low self discharge rates, low serial impedance for medium pulse power demands, negligible voltage delays, guaranteed rated capacity, and reliable definition of end of life (EOL) condition.

Moreover, the system concept of electronic design shall provide power saving modes (e.g. switch-off unused parts, minimize current consumption of permanent powered parts), consume electrical power directly from battery, minimize serial impedances in the power paths, ensure a reliable detection of battery EOL condition, and minimize current consumption during idle mode.

The system concept of mechanical design shall provide actuator system which ensures high efficiency, low starting voltages and simple control, ensure no permanent current consumption, and provide fast and low power position control.

The system concept of wireless communication design shall meet ultra low-power design challenges and ensure low error rates.

The key points to get a high efficient and power saving medical device of the invention were:
  two implantable primary batteries (non-rechargeable); chemistry: Lithium Manganese Dioxide for example
  ultra low power consumption (<6 µA) during idle mode; only few active parts are permanently powered
  design provides several power saving modes (stop mode+ several intermitted modes)
  wireless communication based on medical implant communication service (MICS)—duty cycle sniffing for wake-up
  actuator system based on high performance DC motors, combined with gear box and lead screw deliverable as a compact unit
  gear box with self-retention ensures powerless hold
  detection of lead nut position (travel measurement) with a Hall sensor for precise measurements and lowest current consumption due to the self-locking lead screw design as described above.

The medical device of the invention can comprise only one actuator, the transmission means being designed to transmit the forces induced by the actuator to each of the contractile elements of the structure.

In other embodiments, the medical device can comprise several actuators, each actuator being associated, via appropriate transmission means, to one or several contractile elements.

The artificial contractile structure may be a structure comprising separate contractile elements described above or linked by a support.

In some embodiments, the artificial contractile structure may comprise at least two contractile elements, which can be independent or distributed along a support, in order to be able to reduce the volume of the organ to be contracted in at least two distinct regions of said organ. The device may comprise at least two actuators respectively linked to their corresponding contractile element by their corresponding transmitting means. Each contractile element is able to contract a portion of the organ and to be activated or in a resting position independently of the position of the other contractile elements.

If the structure comprises several contractile elements, said contractile elements can be designed in such a way that each contractile element is connected to an adjacent contractile element, while remaining flexible one with respect to the other. That means that a contractile element and its adjacent contractile element are physically linked or connected to each other, directly or indirectly, by an appropriate connecting element, allowing one to obtain a compromise between the stiffness and the flexibility of the structure. This structure allows applying to minimal pressure to the tissues avoiding tissue necrosis and damage. Moreover, this structure allows optimal pressure control and implantation of the structure by surgeons, by having a single-piece device which is adaptive to the natural flexibility of the urethra while remaining semi-rigid so that the structure stays in place and the pressure of each contractile element can be optimally synchronized.

In some embodiments, the artificial contractile structure may further comprise a first flexible connecting element designed to link each contractile element to an adjacent contractile element, said connecting element being made out of elastic biocompatible material for keeping said contractile elements flexible one with respect to the other. Such first flexible connecting element may be fastened directly to the contractile elements.

More particularly, in some embodiments, said first flexible connecting element is able to keep the contractile elements in longitudinal position while allowing a rotational movement of each contractile element one with respect to the other.

In other embodiments, the artificial contractile structure may comprise two merged contractile elements both elements working independently (one is open while the other is closed). Such contractile elements may be connected by a band of silicone as a flexible connecting element, allowing both elements working independently from each other. Such silicone band has also the advantage that the contractile elements cannot overlap over time.

In other embodiments, two adjacent transmissions means are merged in such a way that the two corresponding adjacent contractile elements are indirectly connected.

In some embodiments, the medical device further comprises at least one second connecting element designed to merge the adjacent transmissions means of two adjacent contractile elements, in such a way that said adjacent contractile elements are indirectly connected via their transmissions means, and more particularly via the cables linking the actuators to the adjacent contractile elements. Such second connecting element may be bars or other similar connecting elements used to merge said two adjacent transmission means. In other embodiments, the transmissions means may be merged by overmolding. In this manner, the contractile elements may be kept in longitudinal position while allowing a rotational movement of each contractile element one with respect to the other.

Advantageously, each contractile element is flexible so that it has the freedom to move longitudinally no more than 5 mm to each direction, preferably no more than 3 mm to each direction, and more preferably no more than 1 mm to each direction from an adjacent contractile element, and so that it can move according to a transversal rotation no more than 30°, to each side, preferably no more than 20° to each side from an adjacent contractile element, allowing the most flexibility and independence of each contractile element from its adjacent contractile elements preventing a peristaltic movement of the whole device along the urethra and allowing optimal synchronization of the contractile elements.

In some embodiments, the control unit may be adapted to pulsatory and alternately activate each contractile element, independently from each other. The actuators are preferably controlled by the same control unit.

In some embodiments, the medical device may further be combined with a device that signals the patient that the contractile structure will open soon, e.g. within next five minutes. This embodiment is preferred if the organ is the bladder, so that the patient has time enough to go to the toilet. The signaling device can be for example a vibration alarm or a LED. The medical device may also further comprise an automated closing feature that the device automatically closes after e.g. 3 min. This has the advantage in case the patient forgets to close.

In the invention, the contractile structure is placed around an organ to be contracted or is placed on (or close to) an organ so that a local pressure is applied to such organ. It may comprise one or more contractile elements disposed around the organ.

A medical device of the invention that has one or more contractile elements placed on an organ (so that a local pressure on such organ is achieved, preferably in a pulsatory manner) may be easier to implant for surgeons, because delicate and/or lengthy surgery around the organ is avoided. In the field of incontinence, this device may however be less convenient for full control of incontinence compared to a device whereby the contractile structure is around the urethra. Such medical device (that has one or more contractile elements on an organ) is however superior to the commercial slings used to control urinary incontinence which have lower success rates (see Retropubic versus Transobturator Midurethral Slings for Stress Incontinence, Holly E. Richter et al. The New England Journal of Medecine, 2010; 362:2066-79). Therefore the contractile structure of the medical device of the invention may be designed as a classical sling in terms of shape and dimensions so that a controlled (by the patient) local pressure is applied on the urethra, therefore maximizing control of incontinence. Hereby such device is defined as an "active sling".

This active sling may not be limited by the embodiments of the present invention, meaning that contractile element may be activated mechanically by hydraulic or pneumatic means as described for in the prior art AMS800 device. Preferably, however a source of energy for powering is used, but the energy consumption of said medical device may be even lower than 50 mAh/year for a pressure applied by the contractile element on the organ comprised between 0.1 N/cm$^2$ and 5 N/cm$^2$, for a battery having a volume between 3 cm$^3$ and 20 cm$^3$. Interestingly even a small pressure on the urethra that is managed by an active sling will improve control of incontinence compared to traditional slings.

Preferably, this active sling is adapted to be placed, at least partially, in a female or male patient in one of several locations, i.e., below the pubis bone, so as to lift the urethra from a point below the pubis bone when the patient is standing, into the pubis bone, so as to lift the urethra from a point attached to the pubis bone of the patient, or above the pubis bone of the patient, so as to lift the urethra from a point above the pubis bone when the patient is standing.

The urethra is lifted by reducing the length of the u-shaped traditional sling. Normally the device forms a loop and the adjustment changes the length of the loop to lift the urethra. The loop can have any shape or form that can be used to lift the urethra when placed inside the loop, when implanted. The device forms a loop that is placed around stable tissue. The loop holds up the urethra, when placed inside the loop, when implanted. Preferably, the interconnecting part is a band or a thread, or a plurality of bands or threads connected to each other to lift the urethra.

The control unit and/or power supply unit includes electronics and software designed to:
control and adjust the actuator generating the force transmitted to the contractile element
provide control of the actuator from outside the body through wireless connection optionally recharge the internal battery through wireless connection control the status of the battery provide test and diagnosis support for health care professionals handling of alarm conditions and exceptions.

The control unit comprises a microprocessor that distributes current to actuators so that they activate the contractile elements pulsatory, at the required pressure and at the required frequency.

As described above, said electronics is placed in the first or third hermetically sealed chamber of the control unit, and preferably in the third chamber, separated from the motor and its gearhead.

The microprocessor can be adjusted via remote control individually for each patient regarding pressure and frequency of opening and closing.

Ideally these adjustments can be done after implantation transcutaneously, preferably by a medicinal physician in order to optimize control of volume reduction (such as incontinence leaking). Readjustments can be performed at any time during the life time of the device using a remote control, as described below.

The number of contractile elements to contract can be adapted to the required pressure to apply on the organ. For example, in the case of urinary sphincter, the number of contractile elements to open and close can be adapted to the abdominal pressure.

The pressure of the structure on the region of the organ to be contracted may be comprised between 0.1 N/cm$^2$ and 5 N/cm$^2$, and preferably between 0.3 N/cm$^2$ and 2.5 N/cm$^2$.

In a preferred embodiment, the device of the invention comprises:
i) an artificial contractile structure implantable into the human body and comprising one or more contractile elements able to be activated by an actuator as described above,
ii) at least one implantable actuator which upon activation will induce a contraction of the contractile elements, such as the actuators described above,
wherein the actuator and the contractile elements are designed so that the pressure, applied on the organ to be contracted, is comprised between 0.1 N/cm$^2$ and 5 N/cm$^2$, and preferably between 0.3 N/cm$^2$ and 2.5 N/cm$^2$ during a period comprised between 30 seconds and 90 minutes, preferably between 30 seconds and 60 minutes, more preferably between 30 seconds and 45 minutes, and more preferably between 10 minutes and 30 minutes.

Each contractile element is preferably activated or deactivated several times a day, and most preferably several times an hour. The contractile elements may be activated, in a pulsating and alternating manner, a pressure on an organ to be contracted during a period comprised between 30 seconds and 90 minutes, preferably between 30 seconds and 60 minutes, more preferably between 30 seconds and 45 minutes, and more preferably between 10 minutes and 30 minutes. Preferably, the strength is such that the different regions of the organ are completely closed in a pulsating and alternating manner. The relaxation time is dependent on the number of regions which are to be contracted by the independent contractile elements.

If the artificial structure is adapted to contract for example four regions of an organ, and if only one contractile element is activated at the same time, each contractile element can be activated during one minute and deactivated during three minutes in an alternating manner. In another embodiment, each contractile element can be activated during five minutes and deactivated during fifteen minutes in an alternating manner. If the structure is adapted to contract three regions of an organ, each contractile element can be activated during one minute and deactivated during two minutes in an alternating manner. If the structure is adapted to contract two regions of an organ, it comprises two contractile elements, which can be activated during 30 minutes and deactivated during 30 minutes in an alternating manner.

The activation of each contractile element can be random or sequential.

Only one of the contractile elements or several contractile elements can be contracted at the same time. In other embodiments, one contractile element can remain contracted or closed whereas another contractile element is contracted or closed.

Advantageously, the medical device comprises a control unit which is designed so that at least two contractile elements are able to be maintained in the same position at the same time. This feature of the medical device may be used separately or in combination with anyone of the features of the medical device described above.

Preferably, at least two contractile elements are able to be actuated pulsatory and alternately independently from each other and also to be maintained in the same position at the same time. More preferably, at least two contractile elements are able to be maintained in their activated position at the same time, preferably for sport activities of a patient.

If the patient wishes to do sport, several or all the contractile elements may be closed in such a way that the pressure, which is applied on the organ to be contracted, is increased for a certain time, typically 1 h (so called sports mode). After that time the system goes back into the alternately activation controlled by the control unit. To avoid tissue damage sports mode cannot be activated more than twice in a row and not more than maximum 3 hours a day.

Advantageously, the control unit is designed so that at least two contractile elements are able to be maintained in their resting position at the same time, preferably for sleep activities of a patient.

During the night, several or all the contractile elements may be maintained in a resting position, without any contraction in such a way that the energy consumption is reduced.

All these embodiments are obtained by means of an adequate control unit. Said control unit is designed to allow an adjustment of the pressure of the contractile structure on the organ according to the patient's need, by adjusting the force generated by the actuator and the frequency the contractile structures are acting. Advantage is that the physician can customize the optimal pressure of the contractile structure to side effects on the organs, for example by means of a magnet placed around the device. The parameters of the control unit and also of the actuator can be adjusted by the physician after the implantation of the device during the postoperative consultations.

The control of the contractile structure and more especially its opening can be achieved, by the physician or the patient himself, by a manual control of the control unit by means of a remote control to open and close the urethra. The remote control is preferably wireless. For the physician, the remote control can be designed to enable adjustments of the medical device (activation force, parameters of the pulsatory and alternately activation, test and diagnosis mode). An optical signal and/or vibration and or acoustic signal may be provided in order to show the patient the level of the battery status. Two different remote controls can be provided: a simple remote control for the patient and an advanced remote control for the healthcare professionals. The patient gets a simple remote control to open and close the contractile structure and to get some information like battery status and device status. The healthcare professionals have an advanced remote control that in addition allows to readjust the pressure and frequency, move the device into the examination mode as described below (motor will move typically 5 mm in the opposite direction of closing the contractile structure) reading implant parameters.

Advantageously, the medical device of the invention further comprises safety means designed to change automatically the position of the contractile element.

This feature of this medical device may be used separately or in combination with anyone of the features of the medical device described above.

Advantageously, said safety means are designed to move automatically the contractile element from its activated position into its resting position. More particularly, said safety means are designed to move automatically the contractile element from its activated position into its resting position if the pressure applied on the organ is higher than a preset pressure or if the power of the source of energy is less than a preset power.

Advantageously, said safety means are designed to move automatically the contractile element from its resting position into its activated position for example if the time for which the organ is not constricted is higher than a preset time.

For emergency, the control unit may be controlled by means of a switch placed under the skin, which is activated by pressure on one or several buttons. Preferably, the switch comprises several buttons and the sequence for pressing the buttons is predetermined in order to avoid accidental opening of the structure.

Another alternative for safety is a strong magnet used outside the body for moving on the skin to activate the lead screw/nut system, to open the contractile element in case of a mechanical failure (e.g. motor blocked).

Another alternative for safety is the automatic opening of the contractile elements after reaching a certain force (typically 5N) or pressure.

In other embodiments, the control of the contractile structure and more especially its opening can be achieved, by the physician or the patient himself, by a manual control of the contractile elements themselves by means of a releasing device designed to manually open the contractile structure. Such releasing device can be used if the patient lost the remote control or if a surgeon wishes to open the structure to endoscopically examine the patient or if a kidney stone has to be removed. This corresponds to the examination mode (motor will move typically 5 mm in the opposite direction of closing the contractile structure to totally open the contractile structure) allowing the examination with an endoscope without risk of damage of the urethra.

Advantageously, the closed structure of the invention has a diameter comprised between 8 mm and 35 mm. The dimensions of the open structure are such that, when the contractile element(s) of the structure is/are fully open, the surgeon can move an endoscope through the lumen of the urethra/rectum in order to endoscopically examine the patient. In the same way, the dimensions of the open structure are such that, when the contractile elements of the structure are fully open, kidney stone removal is possible.

Preferably, each contractile element is separated from an adjacent contractile element no less than 1 mm to 2 cm, preferably 2 mm to 1 cm, more preferably 2 mm to 8 mm, for avoiding over-compression.

Preferably, the structure of the invention may be comprise between 2 and 8 contractile elements, so that it makes an overall length comprised between 20 mm and 50 mm.

The present invention relates also to a medical device comprising:
- an artificial contractile structure comprising at least one contractile element adapted to contract an organ, in such way that said contractile element is in a resting or in an activated position, the activated position being defined with said contractile element constricting the organ and the resting position being defined with said contractile element not constricting the organ,
- at least one actuator comprising at least one electromotor and transmission means linked to the contractile element and designed to transmit to the contractile element a force induced by said electromotor,
- at least one control unit comprising and controlling said actuator,
- at least one source of energy for powering said actuator.

According to the invention, said actuator comprises an internal magnetic coupling device designed to transmit to the contractile element a force induced by the electromotor.

Said actuator comprises at least an electric motor, a gearhead connected to said electric motor, a lead screw and a nut mounted on said lead screw, one of the nut and the lead screw being linked to said transmission means and the other of the nut and the lead screw being designed to cooperate with said gearhead.

The magnetic coupling device comprises a first magnet designed to cooperate with the gearhead, a second magnet designed to cooperate with one of the nut and the lead screw, and optionally a third magnet which is mounted on a plate supporting the first magnet. The magnets are implanted in the body of the patient.

The actuator further comprises sensors designed to indicate the position of the transmission means.

Advantageously, the sensors are Hall sensors and are placed at the gearhead. This allows to increase the sensitivity of the Hall sensors.

Examples

Referring to FIG. 1, one embodiment of the medical device of the invention, used to treat urinary incontinence, comprises two adjacent contractile elements 100 designed to surround partially a hollow part of the urethra. The contractile elements 100 are indirectly connected by using bars 102, said bars being connecting elements fixed around the transmission means and used to merge said two adjacent transmission means, i.e. the two adjacent cables which are inserted in Teflon® tubes 104 which are covered with silicone (silicone tube or silicone coating).

The contractile element 100 comprises a U-shaped band 106 designed to surround at least one time the hollow part of the organ to be contracted. The band 106 is made of silicone, PTFE, PLA, PUR, PMMA, (POM), HDPE LDPE or combination thereof to reduce the friction when the band wraps closely around the organ.

Figure 2:
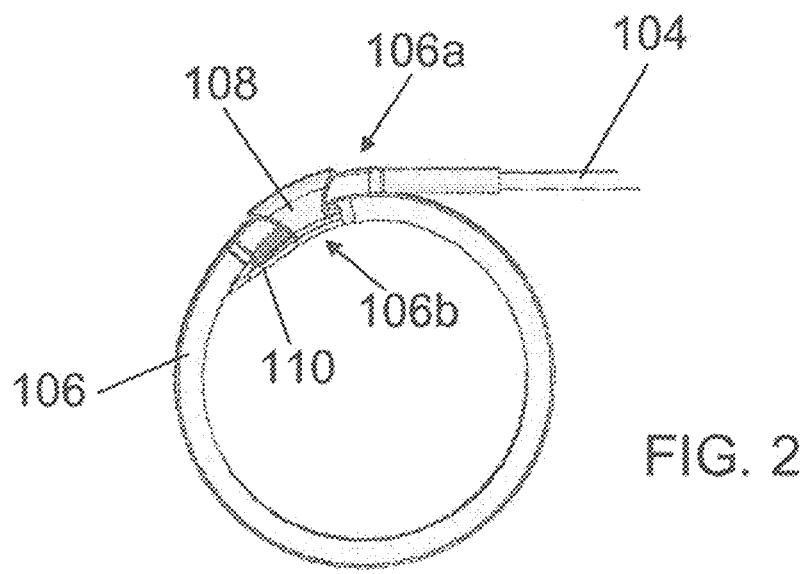
FIG. 2 represents a schematic view of a first embodiment of the contractile element used in the invention.

At shown by FIG. 2, the band 106 comprises a first end 106a, in which the tube 104 comprising the cable, is integrated and a second end 106b, which is free. This free end 106b is made from PEEK, POM or similar biocompatible material which is able to slide through a movable cover acting as a locking member 108 of a click mechanism and made also from PEEK, POM or similar biocompatible material until the position is reached where the band 106 is surrounding the organ without applying any surface pressure to the organ. In this position, the free end 106b of the band 106 is clicked into the locking member 108. The free end 106b of the band 106 is protected with a silicone lip 110 to guarantee that the organ is in contact only with soft silicone.

Figure 3:
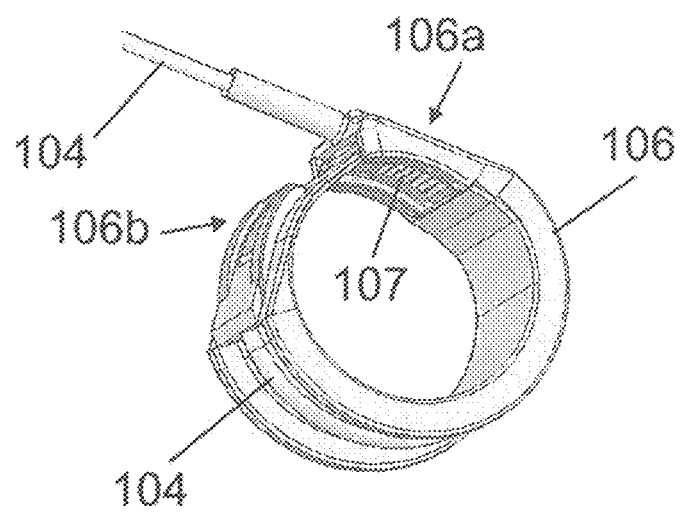
FIG. 3 represents a schematic view of a second embodiment of the contractile element used in the invention.

In another embodiment as shown by FIG. 3, the contractile element 100 comprises locking means which are a snap mechanism. The free end 106b of the U-shaped band 106 is designed to cooperate with a grid 107 provided on the other end 106a of the band 106 to close the contractile element 100.

The medical device comprises also two actuators placed in a box 112 away from the organ to be contracted. Each actuator is linked to the corresponding contractile element 100 by the corresponding cable in the corresponding tube 104.

A control unit 114 is used to control and activate the contractile element 100 shown in FIGS. 1 and 2. The control unit 114 is placed in a box 112 made of titanium.

Figure 4:
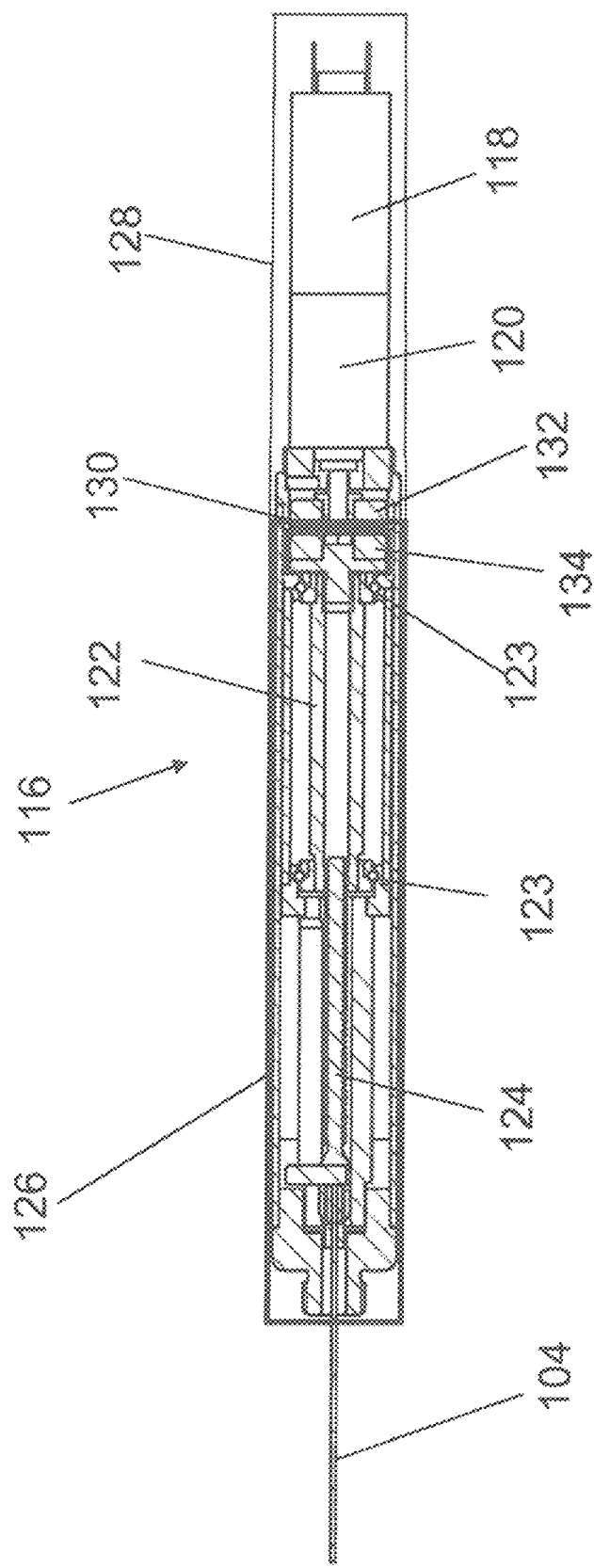
FIG. 4 is a schematic view of an actuator used in the invention.

FIG. 4 shows one of the actuators 116, said actuator having an electromotor comprising an electric motor 118, a gearhead 120 connected to said motor 118, a lead screw 124 and a rotating nut 122 mounted on said lead screw 124. The nut 122 is a hollow cylinder, in which the lead screw 124 is able to move according to an axial movement. Ball bearings 123 are provided for improving the rotation of the nut 122. The tube 104 and its cable are attached to the center of the lead screw 124, along the lead screw axis. The end of the tube 104 and the cable, the lead screw 124 and the nut 122 are placed in a second chamber 126, which is not hermetically sealed. The motor 118 and the gearhead 120 are placed in a first chamber 128, which is made of titanium and which is hermetically sealed with the second chamber 126 by using the thin titanium wall 130 of the second chamber 126 as a hermetic seal. A first magnet 132 is placed in the first chamber 128 and a second magnet 134 is placed in the second chamber 126, face to face on each side of the hermetic seal 130.

The second magnet 134 is placed at the end of the rotating nut 122 facing to the gearhead 120 and the first magnet 132 is placed on a pin at the end of the gearhead 120. When the motor 118 turns, the first magnet 132 rotates and transmits rotation to the second magnet 134 that rotates the nut 122. The nut 122 transmits the rotational movement into axial movement of the lead screw 124 and finally the cable in the tube 104 that transmits the force to the corresponding contractile element 100 to close or open it.

The cable is woven out of several bars or one single bar and is made of stainless steel, titanium or polymer and inserted in the tube 104 made of Teflon®.

The control unit 114 comprises also a printed circuit board to control the actuators 116 and a position Hall sensor which are placed outside the second chamber 126 close to the second magnet 134.

Figure 6:
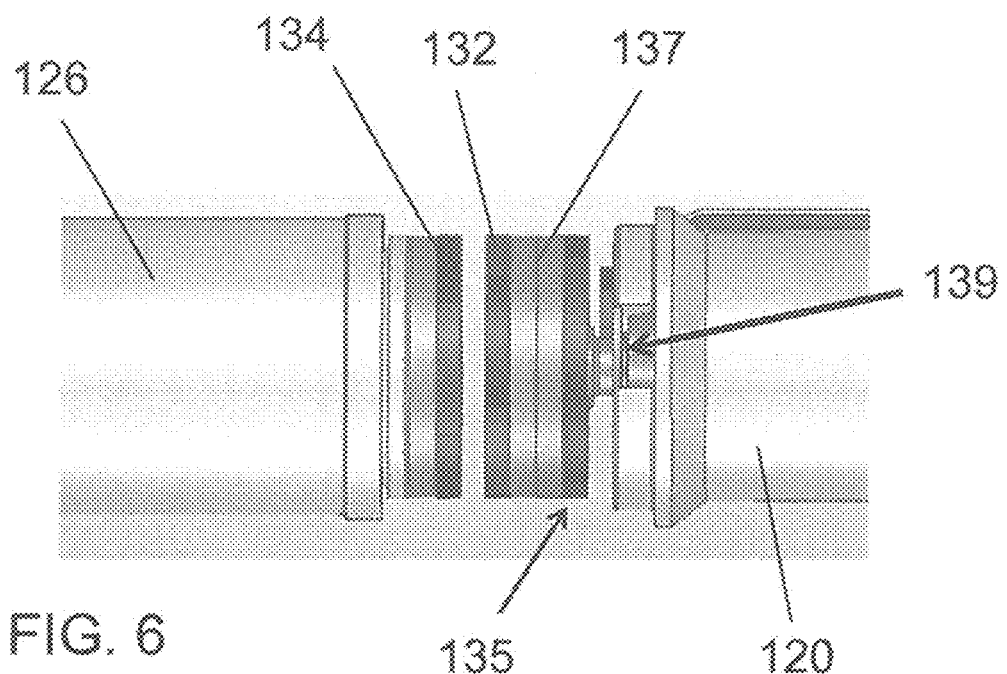
FIG. 6 is a detailed side view of a preferred embodiment of the magnetic coupling device.
Figure 7:
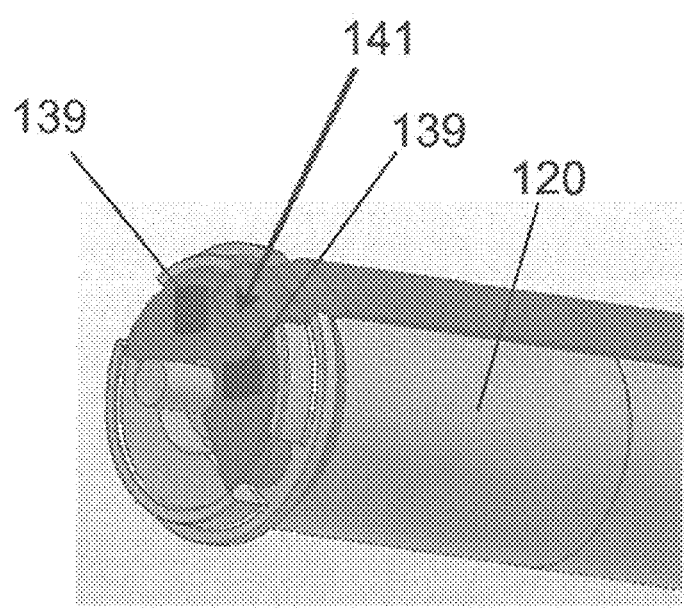
FIG. 7 is a detailed perspective view of a preferred embodiment of the magnetic coupling device.

In another preferred embodiment as shown by FIGS. 6 and 7, a third magnet 135 is mounted on a metal plate 137 that shields magnetic fields from the first magnet 132. This metal plate 137 is the support for the first 132 and third 135 magnet. This third magnet 135 is used for the position sensing by using for example two Hall sensors 139 which are placed in a third chamber at the front of the gearhead 120. The Hall sensors 139 are mounted on a flex PCB 141.

As shown by FIG. 1, the control unit 114 is separated from the energy source. The energy source is in the power supply unit 140 that is connected to the control unit 114 by two electric cables 142, which are easily detachable by using connectors 144. The energy source comprises two implantable primary (i.e. non-rechargeable) batteries, each having a lifetime of at least 4 years for a volume of 3.7 cm$^3$. In another not shown embodiment, the batteries may be in sequence instead of in parallel. Therefore, only one electric cable and only one connector can be used.

In case of power loss the control unit comprises a capacitor which has enough energy stored to apply to the electromotors and to open the contractile elements 100.

Almost no energy is needed to maintain the contractile element 100 in its activated position due to the self-locking characteristics of the lead screw/nut combination. Only a few electronic components are permanently powered.

The control unit is adapted to distribute current to each actuator, preferably in order to pulsatory and alternately contract the contractile elements 100.

In this case, there are several gates which can be independently, pulsatory and alternately activated in order to contract one or the other region around which the contractile elements 100 have been placed, in a pulsating and alternating manner. This allows an alternate contraction along the urethra, several times an hour. Such a configuration avoids stressing of the underlying tissue followed by erosion and necrosis.

The control unit is designed to activate at least one actuator and therefore to activate at least one contractile element so that at least one region of the urethra is closed to avoid incontinence. The patient deactivates the device if necessary, so that each actuator is inactivated to open each region of the hollow part of the urethra, allowing the passage of the urine.

There are also means for opening on demand said artificial contractile structure, used by the physician or the patient himself to inactivate the actuators and open the contractile elements.

The device can further comprise sensing means selected from pressure, and force sensing means.

Obviously, the device of the invention can be used with a control unit adapted to drive the contraction of the contractile elements, on demand, without pulsatory and alternately contracting said contractile elements.

The operating time of the medical device as shown by FIG. 1 was tested for different travels of the lead screw 124 and for different cycle times.

The travel is the distance covered by the lead screw 124 in such a way that the contractile element 100 moves between its resting and activated positions. A cycle time comprises movement of the lead screw for closing the contractile element, time for which the contractile element is closed, movement of the lead screw for opening the contractile element and time for which the contractile element is opened.

The travels were 8 mm and 4 mm. The cycle times were 10 minutes, 20 minutes and 30 minutes.

The electromotor comprised the motor 0816006S from Faulhaber, lead screw pitch is 2.29 mm and the diameter is 2.00 mm; gear ratio is 9:1.

The control unit comprises as source of energy two primary batteries of 1.1 Ah, with an assumed shelf life of 1 year, for a volume of 3.7 cm$^3$ each.

The pressure applied by the contractile element on the organ was 1.5 N.

Figure 5:
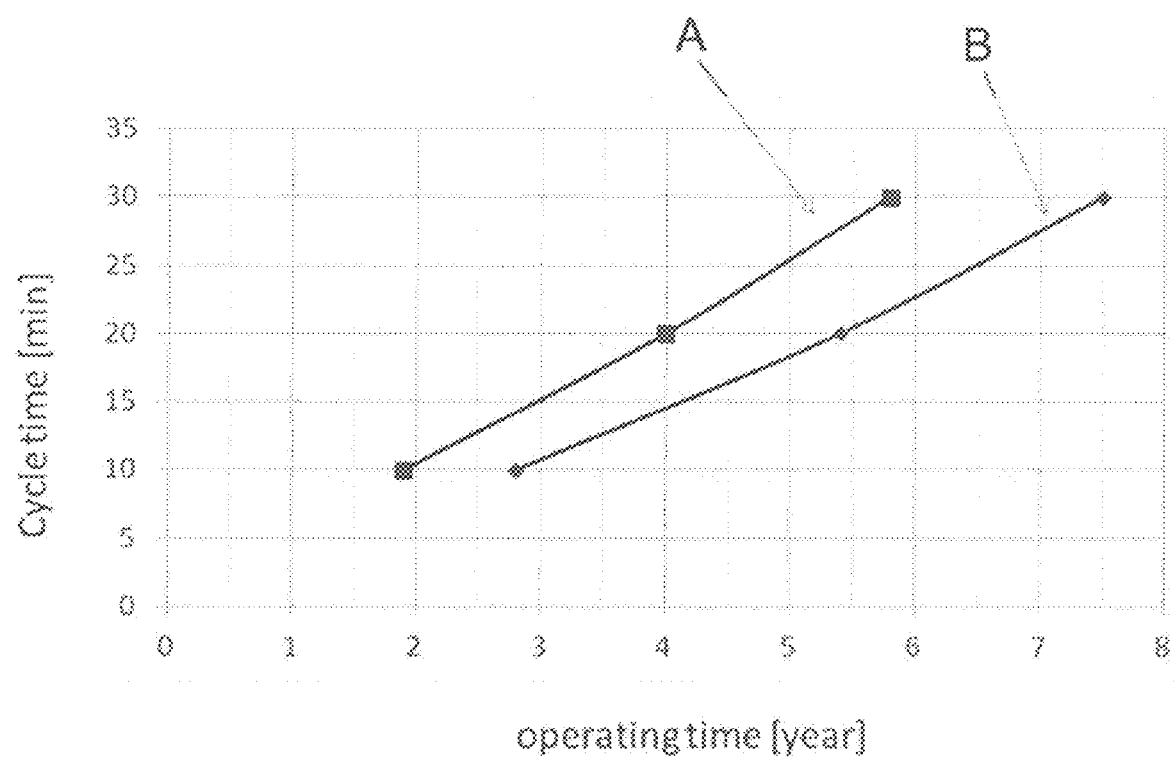
FIG. 5 represents the cycle time as a function of the operating time for a device of the invention using primary batteries.

The results are shown by FIG. 5, which represents the cycle time as a function of the operating time for different travels for a travel of the lead screw of 8 mm (curve A), and a travel of 4 mm (curve B). FIG. 5 shows that the medical device of the invention allows to use primary batteries enabling to obtain an operating time of 1.8 years to 7.5 years.

Moreover, such a medical device allows applying minimal pressure to the tissues thereby avoiding tissue necrosis and damage, even if each contractile element applies a pressure at a frequency of 30 to 45 minutes alternately with the other contractile elements. That means that every contractile element is closed for 30 to 45 minutes alternately with the other contractile elements. A device as AMS 800 shows erosion because the device is closed for about 6 to 8 hours per night and during the day for about 4 hours, assuming that the patient goes every 4 h to the toilet.

The invention claimed is:

1. A medical device comprising:
   an artificial contractile structure comprising at least one contractile element configured to contract an organ such that said contractile element is in a resting position or in an activated position, the activated position being defined with said contractile element constricting the organ, the resting position being defined with said contractile element not constricting the organ, the contractile element comprising a band which at least partially surrounds the organ to be contracted, the band comprising a free end configured to cooperate with a locking system configured to adjust the band to the size of the organ, the locking system comprising a click mechanism, the free end of the band being configured to slide through a movable cover forming a locking member until the resting position is reached;
   at least one actuator configured to activate the contractile structure;
   at least one controller comprising and controlling said actuator; and
   at least one source of energy configured to power said actuator.

2. The medical device according to claim 1, wherein said locking system is configured to adjust the band so that the contractile element reaches the resting position where the band is surrounding the organ without applying any surface pressure to the organ.

3. The medical device according to claim 1, wherein the locking system is configured to fix the free end of the band to another part of the band, said band forming a loop around the organ.

4. The medical device according to claim 1, wherein the free end of the band is clicked into the locking member.

5. The medical device according to claim 1, wherein the free end of the band is protected with a lip.

6. The medical device according to claim 5, wherein the lip is made of silicone.

7. The medical device according to claim 1, wherein the free end of the band is undercut allowing the movable cover to be clicked.

8. The medical device according to claim 1, wherein one or more of the free end of the band and the locking member is made from Polyether ether ketone (PEEK), Polyoxymethylene (POM), or a biocompatible material other than PEEK and POM.

9. The medical device according to claim 1, wherein said actuator comprises at least an electromotor, and transmission system linked to the contractile element and configured to transmit to the contractile element a force induced by said electromotor.

10. The medical device according to claim 9, wherein the transmission system is configured to be linked to and to pull the band, when the contractile element is activated by the actuator, such that the contractile element reaches the activated position.

11. The medical device according to claim 9, wherein the band comprises an end linked to the transmission system coming from the actuator.

12. The medical device according to claim 1, wherein the free end of the band is protected with a lip.

13. The medical device according to claim 2, wherein the locking system is configured to fix the free end of the band to another part of the band, said band forming a loop around the organ.

* * * * *